United States Patent
Brovold et al.

(10) Patent No.: US 9,234,824 B1
(45) Date of Patent: Jan. 12, 2016

(54) GYRATORY COMPACTOR APPARATUSES AND ASSOCIATED METHODS

(71) Applicants: Test Quip, Inc., Solon Springs, WI (US); Troxler Electronic Laboratories, Inc., Research Triangle Park, NC (US)

(72) Inventors: Thomas Brovold, Solon Springs, WI (US); Robert Ernest Troxler, Raleigh, NC (US)

(73) Assignee: Troxler Electronic Laboratories, Inc., Research Triangle Park, NC (US)

(*) Notice: Subject to any disclaimer, the term of this patent is extended or adjusted under 35 U.S.C. 154(b) by 0 days.

(21) Appl. No.: 14/214,287

(22) Filed: Mar. 14, 2014

Related U.S. Application Data

(60) Provisional application No. 61/785,291, filed on Mar. 14, 2013.

(51) Int. Cl.
*G01N 3/32* (2006.01)
*G01N 3/08* (2006.01)

(52) U.S. Cl.
CPC ........................................ *G01N 3/08* (2013.01)

(58) Field of Classification Search
None
See application file for complete search history.

(56) References Cited

U.S. PATENT DOCUMENTS

| | | | |
|---|---|---|---|
| 5,939,642 A | 8/1999 | King et al. | |
| 6,405,602 B1 * | 6/2002 | Itou et al. | |
| 6,492,641 B1 | 12/2002 | Dep et al. | |
| 6,729,190 B1 * | 5/2004 | Boyko et al. | |
| 6,868,738 B2 | 3/2005 | Moscrip et al. | |
| 7,121,149 B2 | 10/2006 | Verna et al. | |
| 7,239,150 B2 | 7/2007 | Troxler et al. | |
| 7,360,444 B2 | 4/2008 | Verna et al. | |
| 7,370,574 B2 | 5/2008 | Verna et al. | |
| 7,705,614 B2 | 4/2010 | Troxler et al. | |
| 8,001,845 B2 | 8/2011 | Caulfield et al. | |
| 8,082,801 B2 | 12/2011 | Caulfield et al. | |
| 8,185,344 B2 | 5/2012 | Troxler et al. | |
| 8,299,808 B2 | 10/2012 | Troxler | |
| 8,359,900 B2 | 1/2013 | Caulfield et al. | |
| 8,400,168 B2 | 3/2013 | Troxler et al. | |
| 2002/0157454 A1 * | 10/2002 | Shimada et al. | |
| 2003/0192384 A1 | 10/2003 | Verna | |
| 2004/0020306 A1 | 2/2004 | Moscrip et al. | |
| 2004/0079166 A1 | 4/2004 | Moscrip et al. | |
| 2005/0021285 A1 | 1/2005 | Troxler et al. | |
| 2005/0022608 A1 | 2/2005 | Moscrip | |
| 2007/0017298 A1 | 1/2007 | Verna et al. | |
| 2010/0281995 A1 | 11/2010 | Caulfield et al. | |
| 2012/0227475 A1 | 9/2012 | Troxler | |
| 2012/0304763 A1 | 12/2012 | Troxler | |
| 2013/0062579 A1 | 3/2013 | Troxler | |
| 2013/0118270 A1 | 5/2013 | Caulfield et al. | |
| 2014/0009170 A1 | 1/2014 | Troxler | |

* cited by examiner

*Primary Examiner* — Lisa Caputo
*Assistant Examiner* — Brandi N Hopkins
(74) *Attorney, Agent, or Firm* — NK Patent Law, PLLC

(57) ABSTRACT

A gyratory compactor apparatus is provided that is adapted to interact with a mold that defines a mold axis. The gyratory compactor apparatus includes a frame that defines a frame axis and has a first mounting plate and a spaced-apart second mounting plate. A pivoted support is carried by the frame and capable of rotation in at least a first and a second rotational degree of freedom. A mold-engaging device is carried by the pivoted support and has a first carriage plate proximal the pivoted support and a second carriage plate axially spaced-apart from the pivoted support for receiving the mold therebetween. At least one actuator having a first end is carried by the frame and a second end is carried by the second carriage plate for imparting lateral translation to the second carriage plate relative to the frame axis. An associated method is also provided.

21 Claims, 6 Drawing Sheets

GYRATORY COMPACTOR APPARATUSES AND ASSOCIATED METHODS

CROSS-REFERENCE TO RELATED FIELDS

This application claims priority to U.S. Provisional Patent Application No. 61/785,291 entitled Gyratory Compactor Apparatuses and Associated Methods filed on Mar. 14, 2013, the entire contents of which are hereby incorporated by reference herein.

TECHNICAL FIELD

The presently disclosed subject matter relates to gyratory compactor apparatuses and associated methods. More particularly, the presently disclosed subject matter relates to improved gyratory compactor apparatuses and associated devices and methods.

BACKGROUND

In order to measure certain physical properties, such as density, modulus, and moisture content and compressive strength of some materials such as soil or paving material, loose samples of the soil or paving material are formed into test specimens under reproducible conditions using laboratory compaction machines. In order to replicate actual expected conditions, it is desirable to compact the test specimens under conditions that simulate actual use. For a paving material sample, this requires simulation of the kneading force applied to the paving material by a paving roller, such as rollers with smooth or sheeps/pad-foot drums or pneumatic wheels, or vibratory compactors such as those used in intelligent compaction. Simply applying a compressive force to the sample does not adequately simulate the kneading action of the paving roller, as the paving roller also applies a shear force to the material being compacted. As a result, compaction machines that apply an orbital motion to the paving sample during compression have been developed to simulate actual conditions of use. For simplicity of implementation and analysis, the orbital motion in many current compaction machines has been restricted to gyration along a circular orbit.

The combination of shear and compaction effort applied to the gyrating specimen is designed to imitate or simulate the kneading effect of in-situ compaction of a material using a rolling compactor.

Various disadvantages have been associated with previously developed gyratory compactors. For example, some gyratory compactors include a ram that is applying compressive force from one end of a cylindrical mold, while the other end of the mold is gyrated by rotating a base supporting the other end of the mold. However, these machines could not easily determine and maintain a consistent angle of gyration due to inconsistencies during rotation of the base, supporting the opposite end of the mold, and flexure of the gyratory compactor during operation. Current implementations further include the use of a mechanical interference to constrain the shape of the gyration motion.

Another example of a gyratory compactor apparatus is disclosed in U.S. Pat. No. 5,939,642 to King et al. (the '642 Patent). The '642 Patent describes a gyratory compactor apparatus design for facilitating ergonomics and efficiency, while improving consistency of operating parameters. The gyratory compactor described therein allows the user to slide the cylindrical compaction mold into the compaction chamber without the necessity of lifting the mold. In addition, the compactor of the '642 Patent includes an integral specimen removal ram, which facilitates easy removal of the specimen from the mold. In addition, the frame design reduces frame deflection that could undesirably affect the angle of gyration. Further, the angle of gyration of the compactor apparatus can be changed by simply replacing a single component of the apparatus. Notwithstanding the advances that have been made in the art of gyratory compactors, there is a need for smaller and less costly designs, with improved operational efficiency and accuracy. Additionally, there is a need for a gyratory compactor having improved ergonomics. For example, placement and removal of the mold containing the sample should be accomplished with minimal difficulty. Additionally, it would be desirable to produce a lightweight frame design that also minimizes frame flexure, thus providing more accurate test results. Moreover, it would be advantageous to enable release of water content when the sample material is fully or partially saturated soil or an emulsified asphalt. Also, it would be advantageous to provide a compactor design that allows the user to quickly, easily, dynamically, and/or in real-time change, control, and calibrate operating parameters, such as the angle of gyration, shape of gyration, and ability to control applied axial load. Further, there is a need in the art for a gyratory compactor that provides a constant, precise, and accurate internal angle of gyration during the compaction procedure with minimal deviation therefrom. The main issue is that the current gyratory compactors do not simulate the actual in-situ motion of the aggregate binder mix. This is mainly because of the hard steel boundary in close proximity to the center of the compaction pressure. If a more realistic compaction sample is to be formed, then the confining boundaries of the current gyratory machines must model the real road-compactor in the field. This necessitates a boundary that exerts the proper stress vectors, shear and viscous damping found in an actual half space of the asphalt base continuum as opposed to representing a perfectly rigid structure. The stress and strain of the gyratory boundary should substantially be a faithful representation of the actual field compaction process which depends on the mix design, base, and environment.

SUMMARY

According to one aspect, an apparatus for compacting a construction material specimen is provided. The apparatus includes a frame defining a chamber for receiving the specimen therein, a ram rod or mechanical coupling configured for applying compressive and/or rotational forces to the specimen, and a pressure sealable layer defined within the chamber and enclosing a circumference of the specimen to impart a hoop circumferential stress or force to the specimen and specimen boundary during compression thereof. The pressure sealable layer models on a small scale the actual normal and shear stresses of the actual compactor-asphalt compaction process.

According to one aspect, the apparatus includes a swivel plate on an end of the specimen opposite the ram rod for applying axial forces to the specimen.

According to one aspect, the swivel plate includes an actuator displayed from a pivot point carried by the swivel plate. The actuator is configured to impart swiveling of the swivel plate about the pivot joint.

According to one aspect, the pressure sealable layer includes a rubber membrane or rather an elastic or resilient boundary that defines a loop that receives the material specimen therein.

According to one aspect, the pressure sealable layer extends into engagement with the compressive forces of the ram rod.

According to one aspect, the apparatus includes a pressure source for supplying pressurized fluids to an area within the chamber that is exterior to the pressure sealable layer. Typical fluids may be oil, hydraulic fluid such as Dextron II, water or air. The sealable layer may be cylindrical, or rectangular yielding to the fluidic pressures presented at the boundary modeling actual boundary conditions in the field.

According to one aspect, related systems and methods are also disclosed herein.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
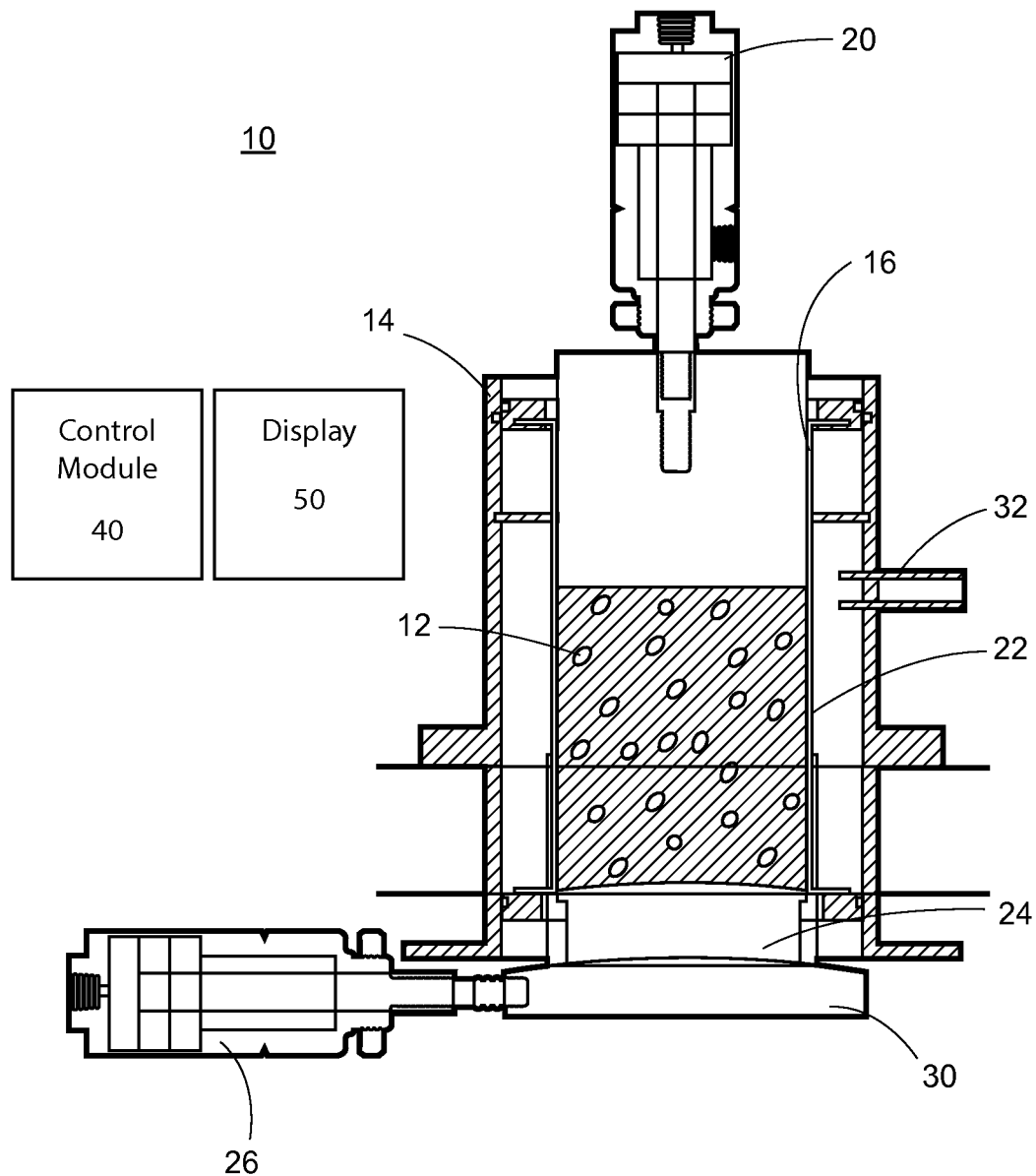
FIG. 1 illustrates a gyratory apparatus according to one or more embodiments illustrated herein.

The presently disclosed subject matter now will be described more fully hereinafter with reference to the accompanying drawings, in which some, but not all embodiments are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

In the field of asphalt testing the specimens are typically made in a gyratory compactor that gyrates a rigid metal mold. Hence, the density is not uniform within the volume and forms a gradient both axially and radially. A serious problem with the specimens made this way is the density difference at the point where the asphalt is in direct contact with the rigid steel of the mold. Hence, the density is not uniform within the volume and forms a gradient both axially and radially. This means that the top and bottom of the specimen, as well as the entire circumference of the specimen have reduced air voids and are not interlocked as one would want the asphalt specimen to be for reproducing and simulating forces acting on asphalt that has been poured in a road surface.

One or more embodiments disclosed herein may be to not have a steel mold in contact with the asphalt specimen on the circumferential sides of the specimen. Asphalt specimens that are tested are typically 100 mm diameter. Gyratory compactors make 150 mm specimens or 100 mm specimens. The density gradient that occurs is the result of the largest aggregate being immovably in contact with the steel. For example, a 19 mm mix will have 19 mm aggregates lined up around the circumference. If a 100 mm specimen was compacted by the gyratory that means 62 mm of the specimens diameter has not been completely afflicted by the steel. For this reason, many times a 150 mm specimen is made and then cored out to obtain a 100 mm specimen with a more uniform density. The top and bottom are typically sawed off to eliminate the density gradient on these ends resulting from the top and bottom rigid steel plate boundaries.

The problem addressed by the one or more apparatuses, systems, and methods disclosed herein is that during construction and normal wear and tear of a road surface, the lateral forces applied to the road may cause movement of aggregate in a generally horizontal or radial direction. Conventional gyratory compactors limit horizontal movement of the aggregate when the aggregate contacts the rigid interior walls of the gyratory mold and, thus, don't replicate true construction dynamics and environmental forces in the horizontal or lateral direction.

Disclosed herein is an apparatus for compacting a construction material specimen, the apparatus being generally designated as 10 and the specimen being generally designated as 12. The apparatus 10 may include a frame 14 that defines a chamber 16 for receiving the specimen 12 therein. A compressive actuator such as a ram rod or mechanically coupled compaction cylinder 20 is configured for applying compressive and/or rotational forces to the specimen 12. The ram rod 20 may apply compressive forces in any appropriately configured manner and may apply forces in a manner that approximates a given function, such as a step function, wave function, sine function, and the like. The ram rod 20 may be of a platen shape, sheep's foot, cylindrical, spherical, rocker, or wheel.

A pressure sealable layer 22 is defined within the chamber 16. The pressure sealable layer 22 is configured to enclose a circumference or perimeter of the specimen 12, meaning to enclose around the specimen 12 in order to impart a hoop compressive force to the specimen 12 during compression thereof. Circumference is not meant to apply only to cylindrical or circular shapes and may be for any perimeter portion of a specimen 12. The pressure sealable layer 22 may be formed from a resilient material, such as, for example, a rubber or polymer based resilient material. In this manner, pressure sealable layer 22 provides a sufficient circumferential stress/force to the specimen so that it maintains, in one illustrative example, a cylindrical shape, but does allow for some lateral translation of granular material in the specimen 12 by translation into the flexible pressure sealable layer 22, where the flexible pressure sealable layer then deforms into an area 28 defined between the chamber 16 and the sealable layer 22 compared to when the sealable layer 22 is not under any external pressure. The pressure sealable layer 22 may be a continuous material to which pressure acts against, or may be a netting or webbing type material that acts to hold the specimen 12 into a cylindrical shape. The layer 22 could be rubber with resilient or elastic bands, or a combination of elastic and inelastic material. In one or more embodiments, the specimen 12 is completely enclosed in a membrane layer 22 with pressure on all sides. The entire membrane could be temperature controlled by applying heating, for example. Stress and strain sensors oriented in several axes may be provided around the sealable membrane for monitoring pressure, force, stress, strain, and temperature for example.

The apparatus 10 may include a swivel plate 24 on an end of the specimen 12 opposite the ram rod 20 for applying axial forces to the specimen 12. The swivel plate 24 may include an actuator 26 displaced from a pivot plane 30 that is carried by the swivel plate 24. The pivot plane 30 may be a pin-hinged assembly, or any other appropriate mechanism. The actuator 26 is configured to impart swiveling of the swivel plate 24 about the pivot plane 30.

The swivel plate 24 may be advantageously provided for inducing shear stress onto the specimen 12. Shear strength describes the magnitude of the shear stress that a specimen can sustain. The shear resistance of soil, aggregate, or asphalt is a result of friction and interlocking of particles, and possibly cementation or bonding at particle contacts. The swivel plate 24 can induce laterally extending stresses into the specimen/sample 12, in conjunction with ram rod 20 which imparts axial strain and stress to the sample 12.

Actuator 26 shown in the examples of the figure is a hydraulic actuator, but in the alternative, the actuators may be an electric, pneumatic, electro-mechanical, piezoelectric, magnetorestrictive or any suitable combination thereof. The extended lengths, forces, and pressures associated with each actuator 26 can be independently set, measured, controlled, displayed, recorded, and transmitted. This control may be accomplished by control module 40.

The apparatus 10 may include a pressure source 32 for supplying pressurized fluids to a volume within the boundaries of chamber 16 that is exterior to the pressure sealable layer 22. In this manner, pressure source 32 acting against sealable layer 22 may impart a hoop compressive stress and may constrain or otherwise define the diameter, circumference, or other dimension defined about the perimeter of the specimen. Pressure source 32 may apply a selectively determined amount of pressure to the chamber surfaces of 16, with the pressure being selectable by communication with control module 40.

Operation of the gyratory compactor apparatus and preparation of the testing specimen will now be described. A suitable sample of material to be compacted is first prepared by mixing appropriate aggregates. Typically, the gyratory compactor apparatus will be used for mixing asphalt. When mixing asphalt, the asphalt composition is heated to a predetermined temperature. The asphalt specimen is not typically heated above 350 degrees Fahrenheit, but in appropriate circumstances may be heated to any suitable temperature depending on the material to be tested. Exemplary methods of preparing asphalt can be found in standards ASTM D6925 or AASHTO T312 included in their entirety. The specimen is then inserted into the specimen receiving area of apparatus 10 and compaction and/or gyration then begins with apparatus 10.

Control module 40 may be provided in communication with the pressure source 32 and a display 50. Control module 40 may have controls for measuring forces applied by the ram rod 20, angle of pivot by swivel plate 24, or any other desired characteristic. Display 50 may be provided for displaying one or more measurements or data from control module 40.

A control module 40 and the various techniques described herein may be implemented with hardware or software or, where appropriate, with a combination of both. The control module 40 may be a circuit board appropriately configured and mounted to apparatus 10. Control module 40 communicates with sensors and systems for power, work, changes in volume, and electrical parameters such as voltage V and current I, sensor outputs such as pressure, differential pressure, stress, strain, and changes in height with respect to changes in diameter with applied pressure and force. These result in the measurement of the elastic parameters such as E, E*, G, G*, v the Poisson ratio with each operational or rotational cycle. Results can be displayed in real time, or transferred to a data base by wire or wirelessly. Further, the control module 40 may be separated from apparatus 10 in the form of a machine such as a computer in communication with components on the apparatus. Thus, the gyratory compactor apparatuses and associated methods of the embodiments disclosed herein, or certain aspects or portions thereof, may be controlled by the control module 40, alone or together, with various other components, executing program code (i.e., instructions) embodied in tangible media, such as floppy diskettes, CD-ROMs, hard drives, or any other machine-readable storage medium. For example, the program code can be loaded into and executed by a machine, such as a computer, and the machine becomes an apparatus for practicing embodiments of the presently disclosed subject matter. In the case of program code execution on programmable computers, the computer will generally include a processor, a storage medium readable by the processor (including volatile and non-volatile memory and/or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

According to one embodiment, the gyratory compactor apparatus can include a display 50 configured to display one of error of the measurement of the actual moment from a target moment, a three-dimensional representation of the actual moment, shear pressure, shear moment, eccentricity, eccentricity vector, or any other information related to moments, information relative to the passing/failing of criteria of target moment information, and average values or information relative to moment. The control module 40 can communicate with the display 50. The display 50 can also display one of the measurement of the actual angle or corresponding error from the prescribed value, the three-dimensional representation of the angle, average angle per gyration. A memory of the control module 40 can store one of the measurement of the actual angle or corresponding error from the prescribed value, the three-dimensional representation of the angle, average angle per gyration, or any information related to angle or internal angle or external angle, or information relative to passing/failing criteria of target angular information, and average values or information relative to angle.

One or more embodiments, may include a rotational member (such as a tire) working against a slab of construction material specimen. A pair of side walls may contain lateral ends of the construction material specimen and end walls contain the other ends of the construction material specimen. A flexible base plate is provided beneath the construction material specimen and floats upon a fluid medium provided beneath. This provides for accommodation of laterally extending forces as also described herein.

Figure 2:
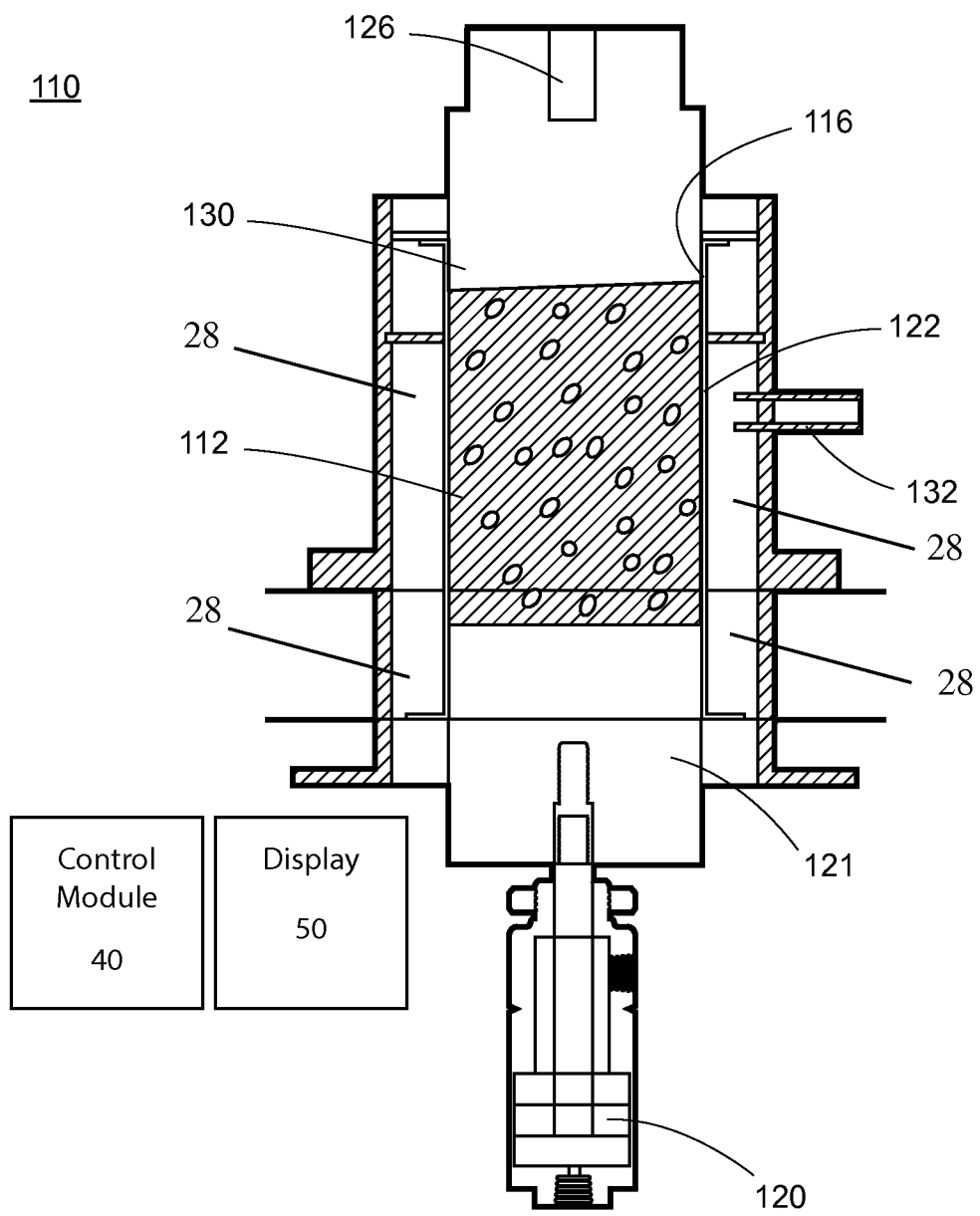
FIG. 2 illustrates a gyratory apparatus according to one or more embodiments illustrated herein.
Figure 3:
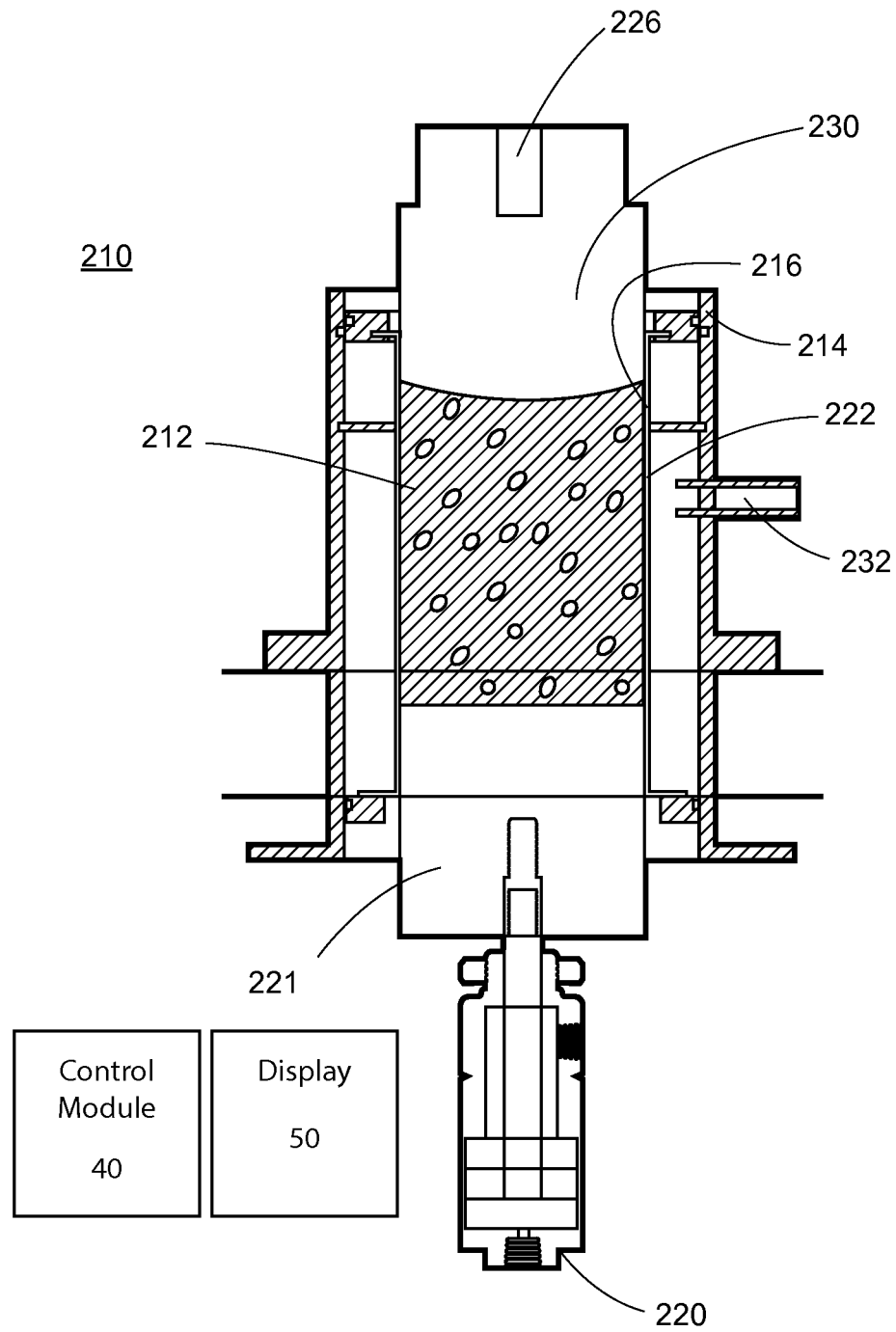
FIG. 3 illustrates a gyratory apparatus according to one or more embodiments illustrated herein.

One or more additional embodiments are illustrated in FIGS. 2 and 3. Each of these embodiments may be in communication with control module 40 and display 50 as set forth with reference to the embodiments illustrated in FIG. 1.

In FIG. 2, an apparatus 110 includes pressure sealable layer 122, similar to sealable layer 22. An actuator 120 applies compressive forces to the bottom of the specimen material 112 via foot 121. A pressure source 132 provides pressure into the chamber to act on pressure sealable layer 122. An actuator 126 having a hub plate 130 contacts the top surface of the specimen material 212. The hub plate 130 has an angle defined about the intersection with specimen 112 and is configured to be rotated by actuator 126 to thereby produce a "wobble" motion.

In FIG. 3, an apparatus 210 includes pressure sealable layer 222, similar to sealable layer 22. An actuator 220 applies compressive forces to the bottom of the specimen material 212 via foot 221. A pressure source 232 provides pressure into the chamber to act on pressure sealable layer 222. An actuator 226 having a hub plate 230 contacts the top surface of the specimen material 212. The hub plate 230 has a curvature defined about the intersection with specimen 212 and is configured to be rotated by actuator 226 to thereby produce a "wobble" motion.

Figure 4:
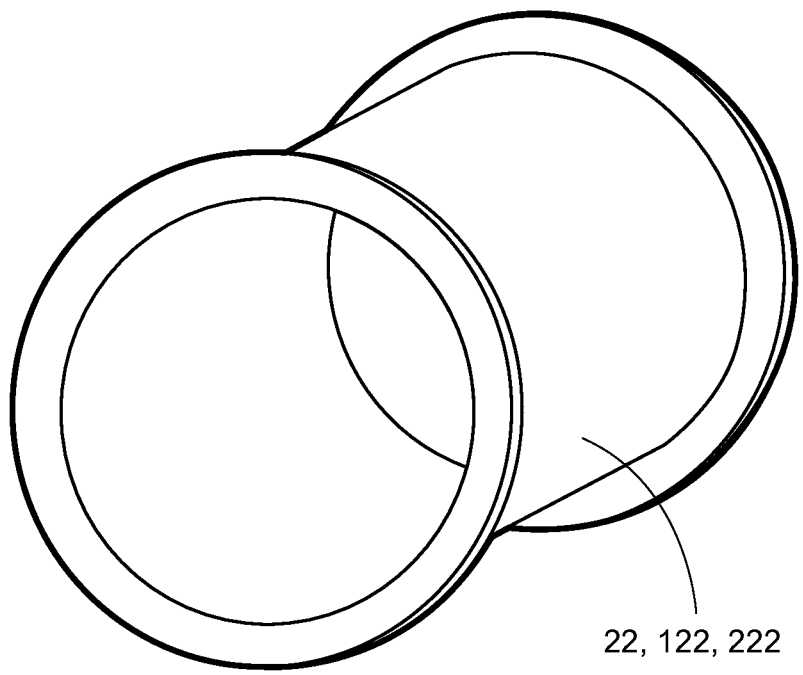
FIG. 4 illustrates a pressure sealable membrane for use with a gyratory apparatus according to one or more embodiments illustrated herein.

A perspective view of the pressure sealable layer 22, 122, 222 as described herein is shown in FIG. 4. The pressure sealable layer is resilient as already described such that pressure acting onto the sealable layer, whether pressure from an outwardly applied pressure source or pressure from radial expansion of a sample during compression can cause a corresponding deflection in the pressure sealable layer. In the example of FIG. 1, this may mean expansion of layer 22 into the cavity 28 during compression and "flattening" of the specimen. Control module 40 may be configured to monitor this deflection in any appropriate manner and direct pressure source to apply a pressure to counteract, either entirely, partially, or in excess of, the pressure being applied by radial expansion of the sample. The layer 22 is illustrated as a cylinder with flanges on each opposing end that are configured extending above and below a portion of the frame of the apparatus 10.

Figure 5:
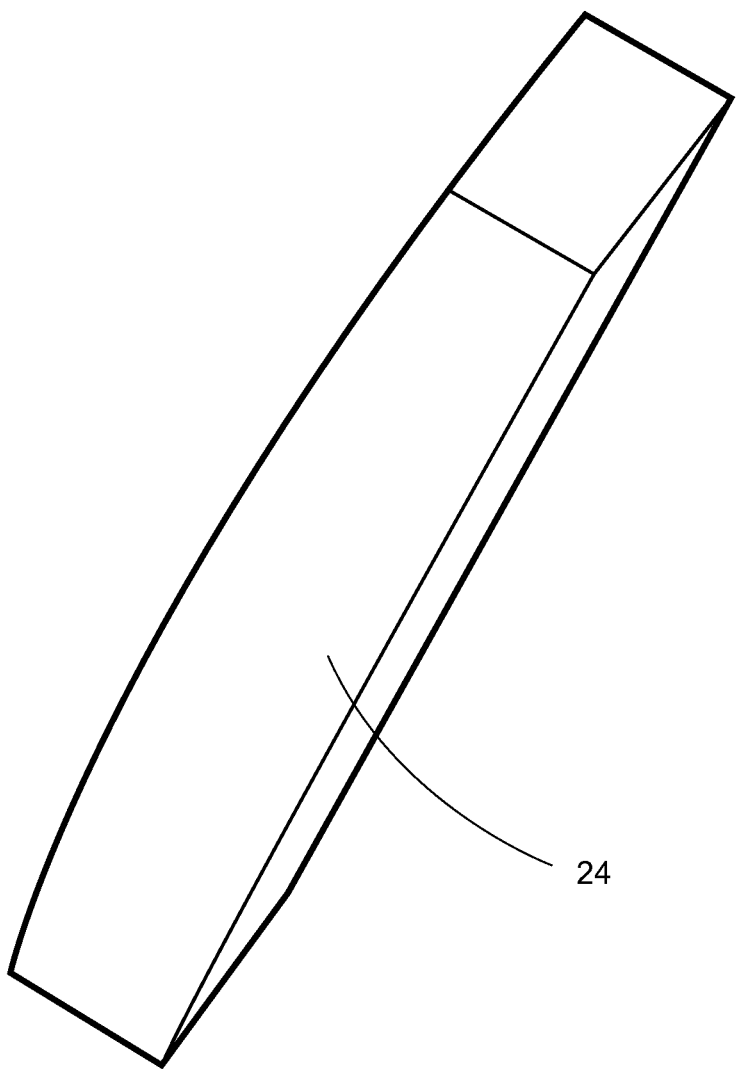
FIG. 5 illustrates a swivel plate for use with a gyratory apparatus according to one or more embodiments illustrated herein.

A perspective view of the compactor drive 24 for use with the compaction cylinder actuator is shown in FIG. 5. Other shapes and configurations may be employed.

Figure 6:
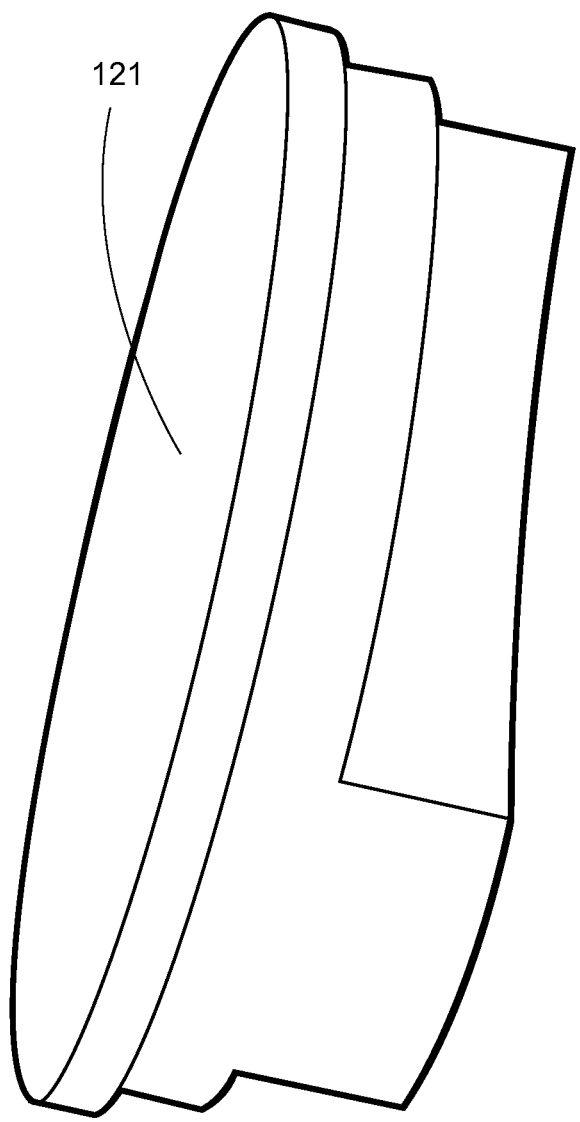
FIG. 6 illustrates a compaction foot for use with a gyratory apparatus according to one or more embodiments illustrated herein.

A perspective view of the compactor foot 121 for use with the compaction cylinder actuator is shown in FIG. 6. Other shapes and configurations may be employed.

One or more embodiments may include using any of the pressure sealable layers disclosed herein to define the diameter of the construction sample. In this manner, the pressure applied from any of the pressure sources disclosed herein may impact the diameter of the construction sample. It has been determined that volume change is critical to the compaction effort. If the diameter is held constant the change in volume is the area of the circle multiplied by the height which can be measured. The work done by the compactor is the change in height times the compaction force. The amount of work energy that the hydraulic or electric motor during compaction is equal to pressure multiplied by change in volume or can be measured directly as the Volts times the Current or Pressure times Flow rate integrated over time. This is the compaction effort to do the work. The power delivered to the system is related to the rate of change of this volume and is linearly related to the electrical complex power delivered in the process or V*I. This calculation is complex because, depending on the loads, there is an angle between the voltage V and the current I. In practical use, there are both mechanical and electrical energy losses and energy storage leading to non-linearities between the mechanical work done and the electrical power delivered. These discrepancies can be corrected for using a calibration routine incorporating regression analysis of known loads such as a roller bearing that is loaded at two or more different loads versus the measured values of voltage, current, time, and sensor outputs such as force, pressure and height. In one or more embodiments, a sinusoidal compaction force in combination with the pressure sealable layer simulates a vibratory compactor.

One advantageous aspect of the one or more devices disclosed herein would be the ability to use the machine that makes the specimens as the machine to run the E* or complex modulus tests on the specimen and with no extra preparation. The AMPT (Asphalt Mixture Performance Tester) runs E* on specimens while under pressure. That is done so the stress field is uniform just like in the roadway. Examples of such machines and example documents are attached and filed herewith, and are incorporated by reference in their entirety.

ASSHTO standards TP 79, PP 60 and PP 61 AASHTO Standards such as:

PP 60—Standard Practice for Preparation of Cylindrical Performance Test Specimens Using the Superpave Gyratory Compactor (SGC)

TP 79—Standard Method of Test for Determining the Dynamic Modulus and Flow Number for Hot Mix Asphalt (HMA) Using the Asphalt Mixture Performance Tester (AMPT)

PP 61—Standard Practice for Developing Dynamic Modulus Master Curves for Hot Mix Asphalt (HMA) Using the Asphalt Mixture Performance Tester (AMPT)

Additionally, U.S. Pat. No. 6,595,068 is incorporated by reference herein.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. An apparatus for compacting a construction material specimen, comprising;
    a frame defining a chamber for receiving the specimen therein;
    a mechanical coupling that applies at least one of shear, compressive, kneading and rotational forces to the specimen; and
    a resilient mold defined within the chamber and enclosing a circumference of the specimen to impart a hoop compressive force to the specimen during compression thereof, the mold and the frame defining an expansion gap therebetween that allows for outward radial expansion of the mold and specimen contained therein.

2. The apparatus according to claim 1, further comprising a swivel plate for applying axial forces to the specimen.

3. The apparatus according to claim 2, wherein the swivel plate includes an actuator defined from a pivot point carried by the swivel plate, the actuator configured to impart swiveling of the swivel plate about the pivot joint.

4. The apparatus according to claim 1, wherein the mold is defined by a rubber membrane that defines a loop that receives the material specimen therein.

5. The apparatus according to claim 1, wherein the mold extends into engagement with the ram rod.

6. The apparatus according to claim 1, further including a pressure source that supplies pressurized fluids to an area within the chamber that is exterior to the mold.

7. An apparatus for compacting a construction material specimen, comprising a frame defining a chamber for receiving the specimen therein;
   a ram rod configured for applying forces to the specimen;
   a resilient pressure sealable mold within the chamber, the mold enclosing a circumference of the specimen to impart a hoop compressive force to the specimen during compression thereof, the mold sized such that an expansion clap is defined between an exterior circumference of the mold and an interior facing surface of the frame to allow for radial expansion of the specimen and mold into the expansion gap; and
   a pressure supply that supplies a selected pressure into the expansion clap to work against the exterior circumference of the mold.

8. The apparatus of claim 7, further including a control module in communication with at least one of the ram rod and the pressure supply.

9. The apparatus of claim 8, wherein the control module is configured to select the pressure applied by the pressure supply.

10. The apparatus of claim 8, further including a swivel plate on an end of the specimen opposite the ram rod for applying axial forces to the specimen, the swivel plate being in communication with an actuator for applying swiveling forces thereto.

11. The apparatus of claim 8, wherein the mechanical coupling and swivel plate are configured for extending into the interior of the mold.

12. The apparatus of claim 8, wherein the control module measures one of pressure and forces applied by the ram rod and the actuator.

13. The apparatus of claim 8, wherein the control module is configured to determine the angle of the hub plate or foot with respect to the mold axis or mold surface normals as a function of time, and a corresponding error from a prescribed values.

14. The apparatus of claim 7, further including a heating source for imparting heating to the sample.

15. The apparatus of claim 7, wherein each surface of the construction material specimen is engaged by one of the ram rod, swivel plate, and resilient pressure sealable membrane.

16. The apparatus of claim 7, wherein the ram rod is configured for extending into the interior of the mold.

17. The apparatus of claim 7, further including a wobble hub for applying shear to the construction material specimen.

18. The apparatus of claim 1, wherein the mold is defined by a rubber membrane that defines a loop that receives the material specimen therein.

19. The apparatus of claim 1, wherein the mold is defined by a resilient membrane that defines a loop that receives the material specimen therein.

20. The apparatus of claim 1, wherein the mold comprises a mold formed from a resilient material, the mold being in communication with a pressure source that applies pressure to an outer circumference of the mold to apply hoop forces that oppose radial movement of material within the mold.

21. An apparatus for compacting a construction material specimen, comprising:
   a frame defining a chamber that receives the specimen therein;
   a ram rod that applies compressive forces along a longitudinal axis to the specimen;
   a resilient mold disposed within the chamber that encloses a circumference of the specimen to impart a hoop compressive force to the specimen when a pressure is supplied against the specimen and during compression thereof;
   wherein the frame and resilient pressure sealable mold define an expansion gap therebetween to allow for radial expansion of the resilient mold;
   a pressure supply that supplies the pressure into the expansion gap to work against an outer circumference of the resilient mold to impart the hoop compressive force to the specimen; and
   a control module in communication with the pressure supply to control an amount of pressure supplied to the expansion gag to work against the circumference of the resilient mold.

* * * * *